United States Patent [19]
Chiu

[11] Patent Number: 5,101,468
[45] Date of Patent: Mar. 31, 1992

[54] LINE FIBEROPTIC LIGHT CONTROL MODULE

[76] Inventor: David Chiu, 33 Roslyn Ct., Port Jefferson, N.Y. 11777

[21] Appl. No.: 681,724

[22] Filed: Apr. 8, 1991

[51] Int. Cl.⁵ .......................... G02B 6/40; G02B 6/36
[52] U.S. Cl. ........................................ 385/115; 128/4
[58] Field of Search ........................ 350/96.24–96.27; 128/4–6

[56] References Cited

U.S. PATENT DOCUMENTS

| | | | |
|---|---|---|---|
| 4,268,116 | 5/1981 | Schmadel et al. | 350/96.29 |
| 4,322,129 | 3/1982 | Takahashi et al. | 350/269 |
| 4,676,593 | 6/1987 | Adachi et al. | 350/96.26 |
| 4,772,093 | 9/1988 | Abele et al. | 350/96.25 |
| 4,824,205 | 4/1989 | Yamashita et al. | 350/96.25 |
| 4,856,495 | 8/1989 | Tohjoh et al. | 128/6 |
| 5,005,943 | 4/1991 | Fort | 350/96.26 |

FOREIGN PATENT DOCUMENTS 2745397 10/1977 Fed. Rep. of Germany ... 350/96.25

Primary Examiner—Akm E. Ullah
Attorney, Agent, or Firm—Leonard Belkin

[57] ABSTRACT

A light intensity control device for an endoscope or similar instrument comprising a light source, a fiberoptic cable connected at one to the light source, and a non-electrical diaphragm assembly connected between the end face of the fiberoptic cable and the end face of the fiberoptic bundle within the endoscope. The diaphragm assembly comprises an adjustable opening for receiving light from the end face of the cable for the transmission of light therethrough. A solid member of transparent material between the adjustable opening and the end face of the fiberoptic bundle within the endoscope transmits the light from the cable to the endoscope.

14 Claims, 4 Drawing Sheets

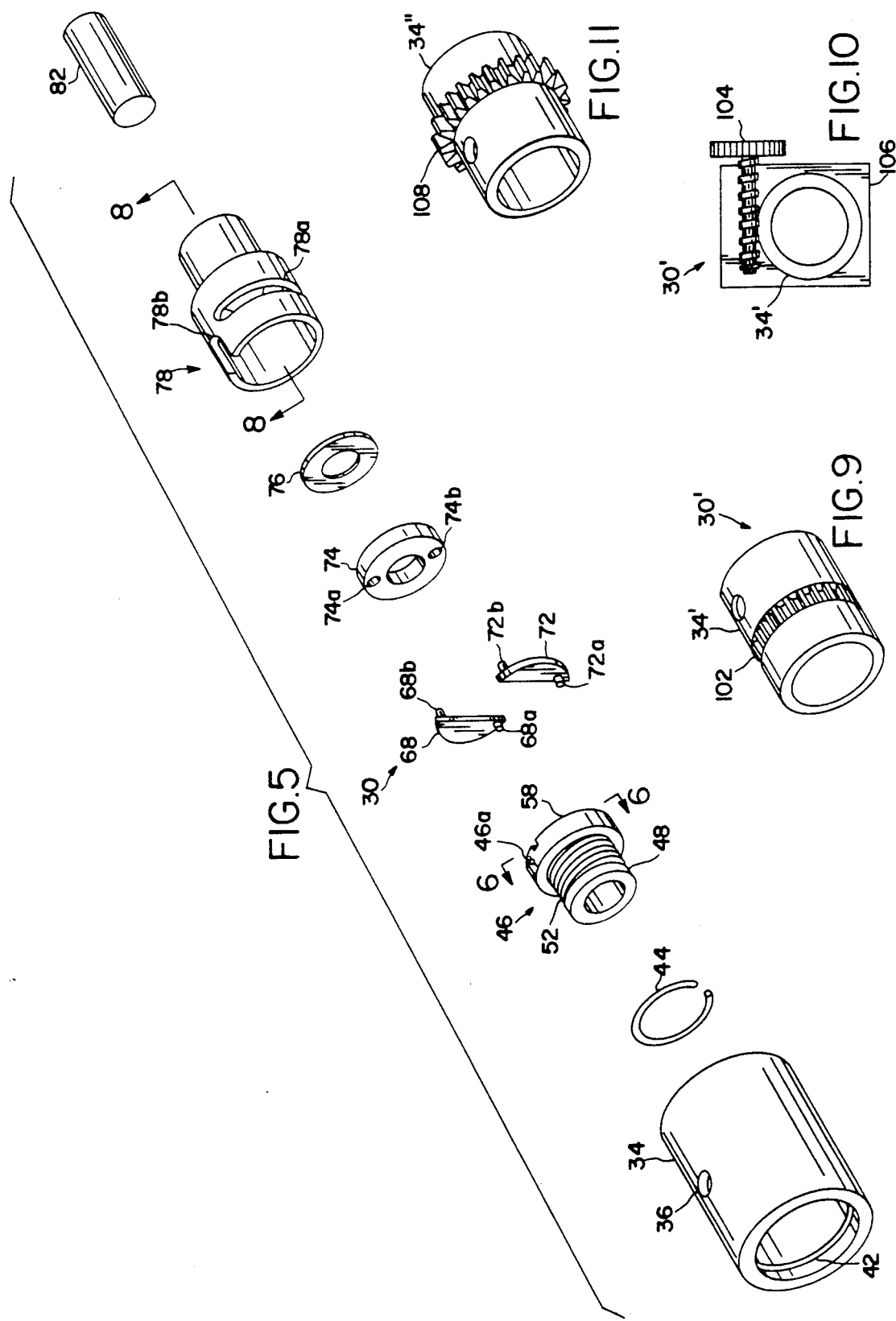

LINE FIBEROPTIC LIGHT CONTROL MODULE

BACKGROUND OF THE INVENTION

The present invention relates to an inline fiber optic light control module and more particularly to an inline fiber optic light control module useful adjacent the point of use without a sacrifice in efficiency.

The usual methods for controlling the light output through an optical fiber optic cable are by adjusting the light with a mechanical diaphragm at the light source itself, or by varying the voltage to the lamp. In certain applications, such as during surgical procedures, an endoscope (such as a laparoscope), usually of metal construction, coupled to the fiber optic cable, may be employed. The surgeon using the device may be anywhere from four to twelve feet away from the source of light. For safety reasons, an electric switch adjacent to the endoscope is not used, so the surgeon must operate while depending on another person to adjust the light source.

When a mechanical diaphragm is inserted between the fiber and the instrument into which it connects, or into the cable itself, there is the problem of aligning the ends of the cable to accept the diaphragm.

A typical cable has 10,000 fibers bundled together in a circular configuration, with dark spots between the circles of glass enclosed in an opaque sheathing forming a fiberoptic cable or bundle. Unless the two ends are perfectly aligned, which is very difficult at best and probably impossible to accomplish, there would be substantial light loss causing a reduction in efficiency and effectiveness.

A number of patents have been issued covering devices which relate to controlling the light in fiber optic cables.

U.S. Pat. No. 4,268,116 shows apparatus for modulating light in optical fibers.

U.S. Pat. No. 4,322,129 discloses a light control device for an endoscope using a shutter mechanism.

U.S. Pat. No. 4,824,205 describes an optical system for providing high quality images from an image guide.

U.S. Pat. No. 4,676,593 illustrates an eyepiece for a fiberscope for rendering inconspicuous the pattern of the cores and claddings of the optical fibers.

U.S. Pat. No. 4,856,495 discloses endoscope apparatus employing a plurality of interchangeable diaphragms to permit selection of the F number which is desired.

German patent 27,45,397 shows in the figures an arrangement for attenuating the light from a lamp to a light carrying cable employing members 7, 8, and 8 which appear to be employed to control the amount of light which is blocked.

None of the aforementioned patents appears to disclose or teach the present invention.

SUMMARY OF THE INVENTION

In the present invention according to a preferred embodiment the light entering a laparoscope or similar instrument is controlled directly adjacent to the instrument. An adjustable iris receiving light from the end face of a fiber optic cable directs the light into a clear, solid transparent member which communicates with the end face of the fiberoptic bundle entering the laparoscope.

Such an arrangement is mechanically simple, economical in construction, and is under the direct control of the person operating the instrument, while at the same time it is highly efficient since much less light is lost than in other systems now in use.

It is thus a principal object of this invention to provide an improved attenuation control system for light in a fiberoptic bundle.

Other objects and advantages of this invention will hereinafter become obvious from the following description of preferred embodiments of this invention.

BRIEF DESCRIPTION OF THE FIGURES

FIG. 5 is an exploded view of the diaphragm illustrated in FIG. 4.
FIG. 9 is an isometric view of an alternative embodiment of the control cylinder.
FIG. 10 is a schematic view of the cylinder shown in FIG. 9 mounted within a housing.
FIG. 11 is an isometric view of another embodiment of the control cylinder shown in FIGS. 9-10.

DESCRIPTION OF THE PREFERRED EMBODIMENTS

Figure 2:
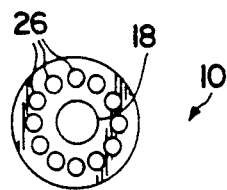
FIG. 2 is a view taken along 2—2 of FIG. 1.
Figure 1:
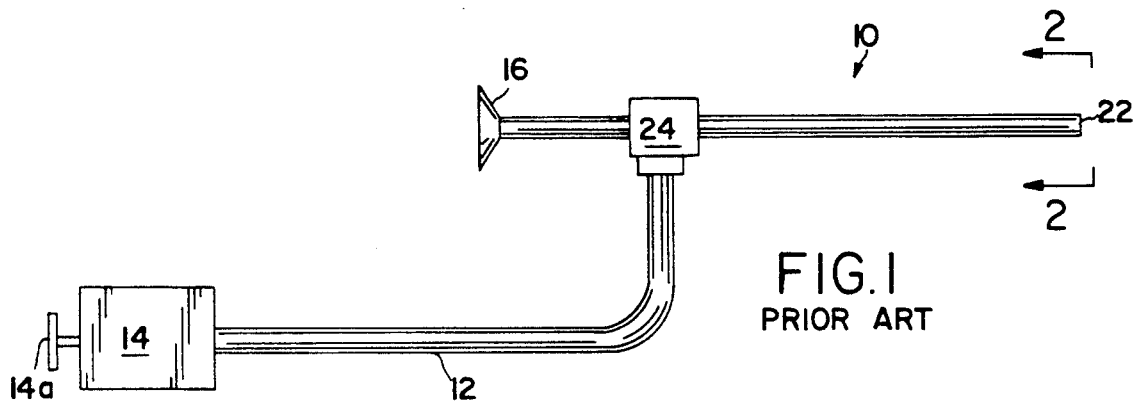
FIG. 1 is a schematic illustration of the prior art.

Referring to FIGS. 1 and 2, a conventional laparoscope 10 is shown connected by a fiberoptic cable 12 to a light source 14 with a dial 14a to dim or otherwise control the amount of light going to laparoscope 10.

As is understood in the art, a laparoscope is an endoscope whose tip is inserted into the abdomen of a person to permit the physician peering through the opposite end to make an examination. Conventional fiber optic cable 12 typically would consist of about 10,000 fibers of glass or plastic transparent material to carry the light from the light source to the instrument.

Laparoscope 10 has an eyepiece 16 through which the physician views the interior of the body. There is a lens system 18 which extends down through the center of scope 10, from eyepiece 16 to distal end 22. Light is brought in from source 14 through cable 12 to transition section 24 of scope 10. Transition section 24 contains the end face of the fiberoptic cable entering scope 10 and distributes the fibers 26 making up the fiberoptic cable around lens system 18 so that at distal end 22 the ends of fibers 22 are annularly arranged around lens system 18 as seen in FIG. 2 to direct light directly into the area being viewed.

As noted earlier, a disadvantage of the system shown in FIG. 1 is that the light source and its control is usually located out of the reach of the physician using the scope.

Figure 3:
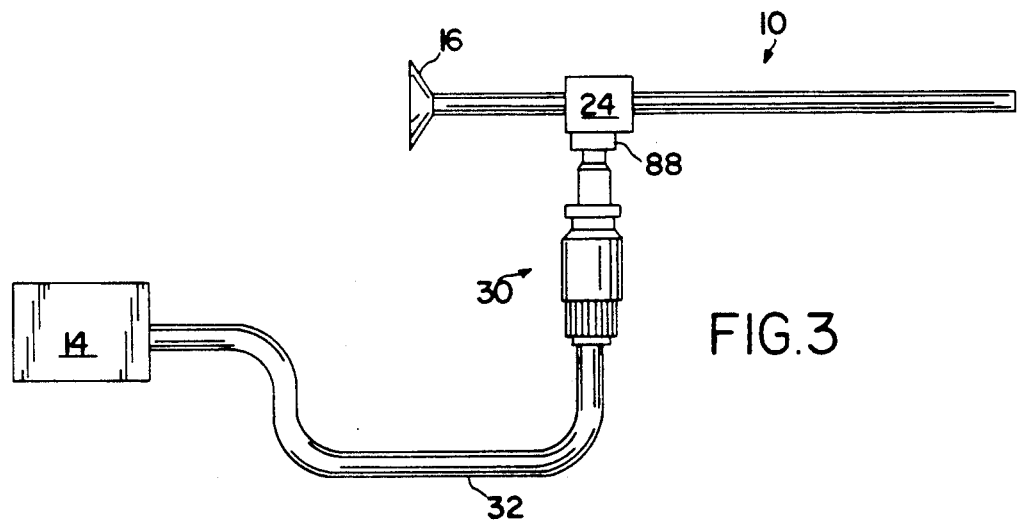
FIG. 3 is a schematic illustration showing a preferred embodiment of this invention.

Referring to FIG. 3, there is shown a light intensity control device consisting of an inline fiber-optic diaphragm assembly 30 embodying the principles of this invention incorporated into a conventional flexible fiber optic cable 32 for permitting control of the light from source 14 to laparoscope 10. Diaphragm assembly 30 would be located adjacent instrument 10 for simple and convenient direct control by the user of the instrument.

Referring to FIGS. 3a, 4, 5, and 6, diaphragm assembly 30 consists of an outer finger tip control cylinder 34 which has an opening 36 to receive a set screw 38 and an internal slot 42 to receive retaining clip 44.

Within cylinder 34 is a stationary diaphragm cam drive member 46 consisting of a hollow cylinder 48 with threads 52 on the outside to accept the threads within connector 54 at the end of fiberoptic bundle 32. The other end of cylinder 48 is provided with an enlarged ring 58 having a face 62 (see FIG. 6) in which a pair of spiral grooves 64 and 66 which are identical, mirror images of each other for a purpose to be described.

For engagement with grooves 64 and 66 there are a pair of flat diaphragm leaves 68 and 72 which have straight sides facing each other and circular outer edges as illustrated. At a common end of each of the leaves is a pin 68a and 72a extending in the same direction, toward its respective grooves 64 and 66 for engagement therewith. The other common ends of leaves 68 and 72 are provided with pins 68b and 72b extending in the opposite direction. A rotatable, hollow diaphragm seat 74 is provided with a pair of sockets 74a and 74b to receive pins 68b and 72b, respectively.

Figure 7:
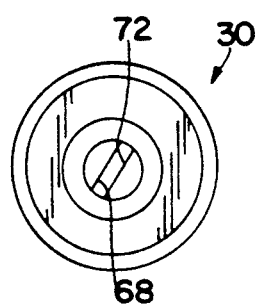
FIG. 7 is a view along 7—7 of FIG. 4.
Figure 7A:
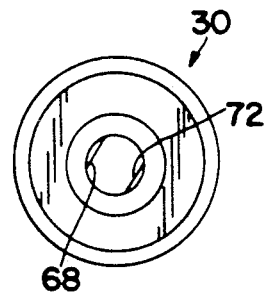
FIG. 7a is a view similar to that of FIG. 7 with a greater opening through the diaphragm.

It will be seen that with diaphragm cam drive member 46 stationary and diaphragm seat 74 rotatable, the space between the straight sides of leaves 68 and 72 can be varied by turning seat 74. In FIG. 7 is shown a small spread, hence, a small opening for light through diaphragm 30 while in FIG. 7a is illustrated a greater opening for the passage of more light.

When diaphragm seat 74 is rotated, it pulls the ends of leaves 68 and 72 with pins 68b and 72b around with it. The other ends of leaves 68 and 72 are also pulled except that pins 68a and 72a which are constrained to ride in grooves 64 and 66 which are shaped to keep the straight sides of leaves 68 and 72 parallel with each other, but the separation between the two is either increased or decreased depending upon the direction of movement of diaphragm seat 74.

Completing the arrangement of diaphragm assembly 30 is a spring washer 76, an assembly body 78, and a transparent quartz rod 82.

Figure 3A:
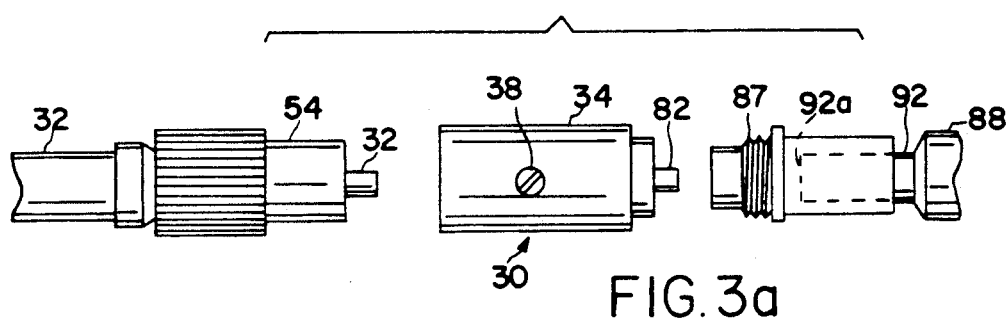
FIG. 3a is an exploded view of the diaphragm assembly shown in FIG. 3 showing how the diaphragm is inserted between the end face of the fiberoptic cable and the end face of the fiberoptic bundle entering the instrument.
Figure 4:
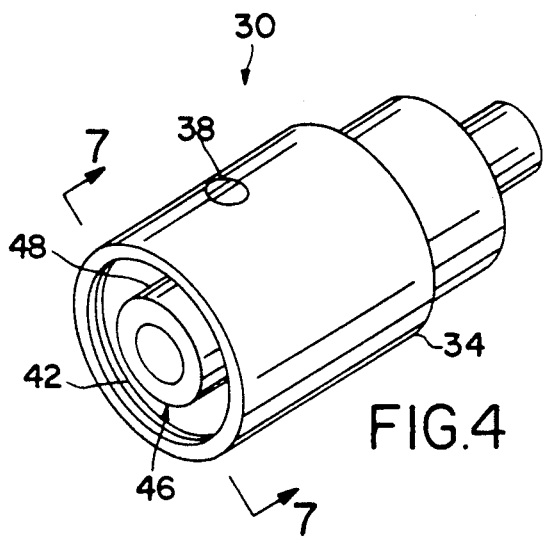
FIG. 4 is an isometric view of the diaghragm used in the system shown in FIG. 3.
Figure 8:
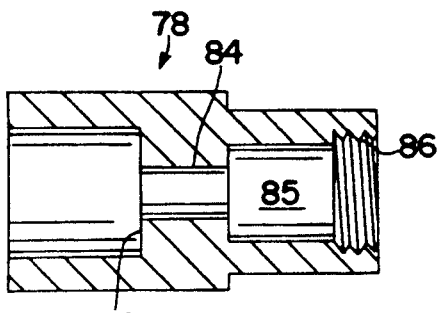
FIG. 8 is a section view taken along 8—8 of FIG. 5.

As also seen in FIG. 8, assembly body 78 is hollow and divided by a partition 82 with an opening 84, and provided with an annular slot 78a to accomodate set screw 38. The length of slot 78a determines the range of opening between leaves 68 and 72. Slot 78b is for a pin to lock body 78 to member 46 using hole 46a. The right chamber 85 is provided with threads 86 to engage threads 87 which are part of connector 88 mounted on one side of transition 24 of laparoscope 10 as shown in FIG. 3a while the other side of partition 82 receives washer 76 and diaphragm seat 74. Transparent quartz member 82 located within chamber 85 provides the light path from the opening between leaves 68 and 72 to the end face 92a of the fiberoptic bundle 92 entering connector 88.

When diaphragm assembly 30 is connected as shown in FIG. 3, the physician using scope 10 can adjust the amount of light delivered by the scope by merely rotating outer fingertip control cylinder 34. Set screw 38 is tightened against diaphragm seat 74 so that they move together. Diaphragm cam drive member 46 is attached to connector 54 as to receive light from the end face of fiberoptic cable 32 and is stationary.

Figure 3B:
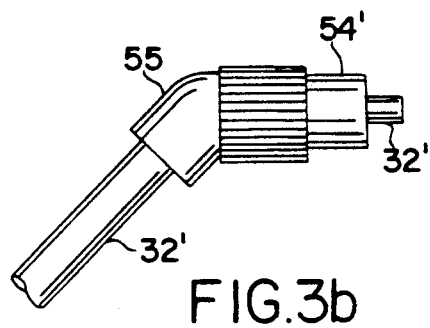
FIG. 3b is a view of the end of the fiberoptic cable having a bend built into the connector.
Figure 6:
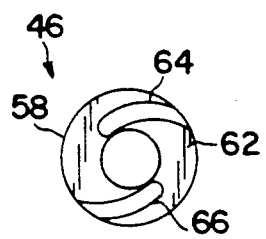
FIG. 6 is a view along 6—6 of FIG. 5.

To render the arrangement more convenient for the physician, referring to FIG. 3b, a connector 54' can be employed which bends the end of fiberoptic cable 34' by a transition piece 55 close to diaphragm assembly 30. In this arrangement illustrated, the bend is 45 degrees but it is understood that another angle may be employed if desired.

Under some circumstances it might be desirable to provide the physician with a thumb screw to turn in order to adjust the opening between leaves 68 and 72 rather than having to rotate cylinder 34 directly by using fingers to do so.

Such an alternative arrangement for rotating cylinder 34 is illustrated in FIGS. 9 and 10. In this arrangement, with cylinder 34' otherwise identical to cylinder 34 previously described, the outer surface is provided with a worm gear groove 102 cut into the outer surface while a thumb screw 104 would be employed to engage worm gear groove 102. In this situation, diaphragm assembly 30' otherwise identical to diaphragm assembly 30 would be mounted within a stationary housing 106 to support thumbscrew 104.

To operate the assembly shown in FIGS. 9 and 10 the physician would merely turn thumbscrew 104 to change the space between leaves 68 and 72 thereby changing the amount of light being delivered to the endoscope.

Figure 11A:
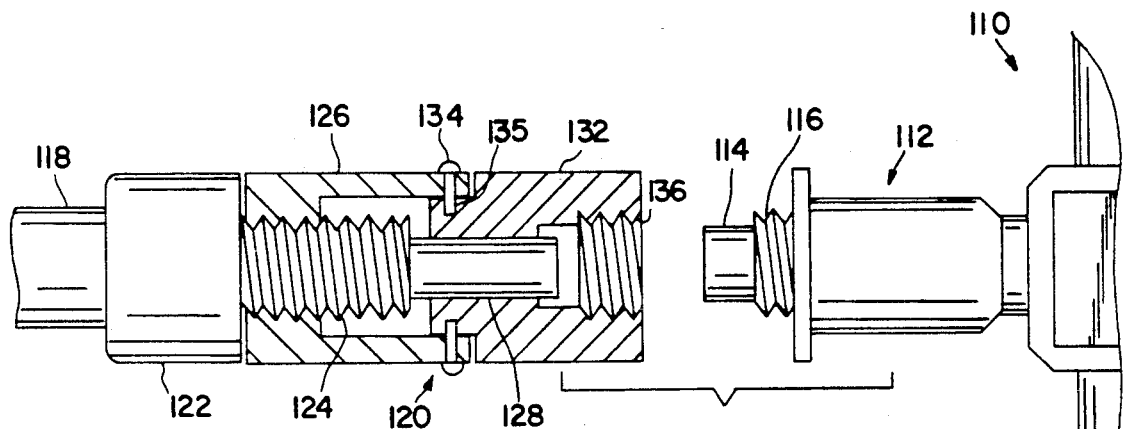
FIG. 11a is an exploded view similar to FIG. 3 partially in section of still another embodiment of the control assembly.

As seen in FIG. 11 cylinder 34" otherwise identical to cylinder 34 can employ a gear ring 108 on the outside of cylinder 34" instead of cutting the groove.

Under some circumstances it might be desirable to employ a light control assembly which is simpler in construction yet reliable.

Such an alternative embodiment of this invention which is simpler in construction is shown in FIGS. 11a–13.

There is illustrated a laparoscope 110 with transition section 112 with the end of fiberoptic cable 114 protruding through a section with external threads 116.

Figure 12:
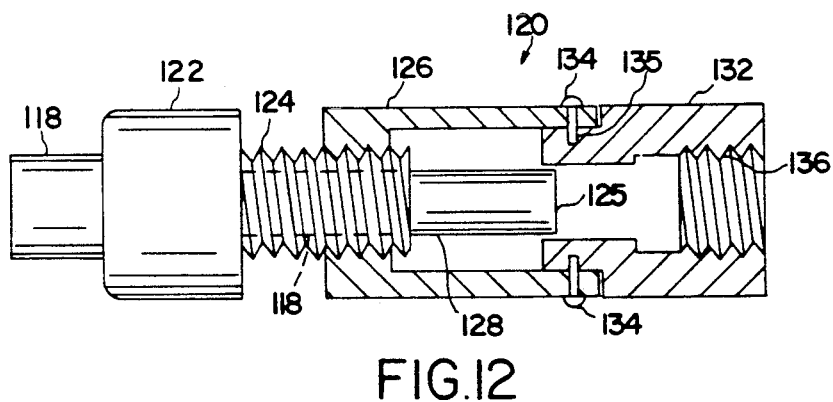
FIG. 12 shows the end of the cable illustrated in FIG. 11 fully retracted.
Figure 13:
FIG. 13 is a section view of the embodiment of FIG. 11 fully assembled.

Fiberoptic cable 118 extending from a light source (not shown) terminates in a light control assembly 120 in which cable 118 terminates. Assembly 120 consists of a stationary transition piece 122 with a male threaded member 124 extending therefrom. Threaded member 124 engages a threaded, rotatable cylinder 126 so that by rotating cylinder 126, threaded member 124 can be fully enclosed within cylinder 126 as shown in FIG. 11 or retracted as shown in FIGS. 12 and 13. The fiberoptic cable 118 without its outer sheathing has an extended portion 128 terminating at end face 125 Connected to threaded cylinder 126 is a hollow stationary adaptor 132 attached at one end by screws 134 riding in a circumferential groove 135 permitting cylinder 126 to be turned to move extended portion 128 of cable 118 so that end face 125 can be moved nearer or further from cable 114.

As will be seen in FIG. 13, by rotating transition member 126 the space between the right end of tube 128 and the end face of cable 114 from endoscope 110 can be varied, in effect controlling the amount of light delivered to scope 110.

It will be seen that there has been provided a simple and non-electrical mechanism conveniently within the reach of the physician using an endoscope for controlling the amount of light being delivered to the area of need. The use of a solid transparent member to transfer the light passing between the diaphragm leaves to the fibers connected to the instrument is an important feature of this invention which avoids the problems inherent in trying to line up the large number of fibers found in such cables.

While only certain preferred embodiments of this invention have been described it is understood that many variations of this invention are possible without departing from the principles of this invention as defined in the claims which follow.

What is claimed is:

1. A light intensity control device for delivering and adjusting the intensity of light to an instrument containing a fiberoptic bundle for receiving light comprising a light source, a fiberoptic cable connected at one end to said light source and terminating in an end face at the other end thereof, and a non-electrical diaphragm assembly connected between the end face of said fiberoptic cable and the end face of the fiberoptic bundle entering said instrument, said diaphragm assembly comprising a mechanical adjustable opening means for receiving light from the end face of said cable for the transmission of light therethrough and a solid member of transparent material between said mechanical adjustable opening means and the end face of the fiberoptic bundle entering said instrument for transmitting the light from said cable to said bundle.

2. A light intensity control device for an instrument containing a fiberoptic bundle for receiving light comprising a light source, a fiberoptic cable connected at one end to said light source and terminating in an end face at the other end thereof, and a non-electrical diaphragm assembly connected between the end face of said fiberoptic cable and the end face of the fiberoptic bundle entering said instrument, said diaphragm assembly comprising adjustable opening means formed by a mechanical diaphragm for receiving light from the end face of said cable for the transmission of light therethrough and a solid member of transparent material between said adjustable opening means and the end face of the fiberoptic bundle entering said instrument for transmitting the light from said cable to said bundle, said diaphragm assembly comprising a hollow stationary cam means connected to the end face of said cable to receive light from said cable for passage through said cam means, hollow rotatable diaphragm seat means for permitting light to pass therethrough, said adjustable mechanical diaphragm being mounted between and connected to both said cam means and said rotatable diaphragm seat means so that rotation of the latter will cause the opening through said diaphragm to change in accordance with the direction of said rotation.

3. The light intensity control device of claim 2 including stationary assembly body means for enclosing said cam means, said diaphragm seat means and said solid body of transparent material, and having means for being attached to the end face of the instrument fiberoptic bundle so that said solid body is in light communication with the end face of the instrument fiberoptic bundle.

4. The light intensity control device of claim 3 having means for effecting the rotation of said diaphragm seat means comprising an outer, rotatable cylinder for enclosing said assembly body, said cylinder including set screw means for engaging said diaphragm seat means for rotating the latter, said assembly body means having a slot in the outer cirumference thereof to accomodate said set screw means.

5. The light intensity control device of claim 4 including stationary housing means for enclosing said rotatable cylinder and including thumbscrew means penetrating said housing for engaging said rotatable cylinder so that rotation of said thumbscrew means will adjust the opening through said mechanical diaphragm.

6. The light intensity control device of claim 4 wherein said mechanical diaphragm comprises a pair of leaves whose separation is controlled by the rotation of said hollow rotatable diaphragm seat means.

7. A non-electrical light intensity control device for an instrument containing a fiberoptic bundle for receiving light comprising a light source, a fiberoptic cable connected at one end to said light source and terminating in an end face at the other end thereof, said fiberoptic bundle extending out of said instrument and terminating in an end face, and means for adjusting the axial distance between said end faces to affect the amount of light being transmitted from said light source to said instrument.

8. The light intensity control device of claim 7 wherein said adjusting means comprises a first member for containing the end face of said cable adjacent the end face of said cable, a second member to support the end face of said fiberoptic bundle, and a third member engaged with said first and second members to permit the space between said fiberoptic bundle end face and the opposite end of said solid member to be varied.

9. The method of controlling the intensity of light delivered to an instrument containing a bundle of optical fibers comprising the steps of connecting one end of a fiberoptic cable to a source of light having an end face at the other end thereof, connecting between the end face of said cable and the end face of said bundle of optical fibers in said instrument a diaphragm assembly comprising adjustable opening means for receiving light from the end face of said cable for the transmission of light therethrough and a solid member of transparent material between said adjustable opening means and the end face of the fiberoptic bundle within said instrument for transmitting the light from said cable to said instrument, and adjusting the size of opening through said diaphragm assembly to control the amount of light passing therethrough.

10. The method of claim 9 wherein said adjustable opening means comprises an adjustable mechanical diaphragm.

11. The method of claim 10 wherein said diaphragm assembly comprises a hollow stationary cam means connected to the end face of said cable to receive light from said cable for passage through said cam means, hollow rotatable diaphragm seat means for permitting light to pass therethrough, said adjustable mechanical diaphragm being mounted between and connected to both said cam means and said rotatable diaphragm seat means so that rotation of the latter will cause the opening through said diaphragm to change in accordance with the direction of said rotation, and rotating said diaphragm seat means to adjust said opening.

12. The method of claim 11 including stationary assembly body means for enclosing said diaphragm cam drive means, said diaphragm seat means and said solid body of transparent material, and having means for being attached to the end face of the instrument fiberoptic bundle so that said solid body is in light communication with the end face of the instrument fiberoptic bundle.

13. The method of claim 12 having means for effecting the rotation of said diaphragm seat means comprising an outer, rotatable cylinder for enclosing said assembly body, said cylinder including set screw means for engaging said diaphragm seat means for rotating the latter, said assembly body means having a slot in the outer cirumference thereof to accomodate said set screw means.

14. The method of controlling the intensity of light delivered to an instrument containing a bundle of optical fibers having an end face to receive light comprising the steps of connecting one end of a fiberoptic cable to a source of light having an end face at the other end thereof, and adjusting the axial distance between said end faces to affect the intensity of light delivered to said instrument.

* * * * *